(12) United States Patent
Khrushchev

(10) Patent No.: US 10,107,473 B2
(45) Date of Patent: Oct. 23, 2018

(54) IRRADIATION APPARATUS HAVING RADIATION UNIT

(71) Applicant: OSRAM GmbH, Munich (DE)

(72) Inventor: Sergey Khrushchev, Regensburg (DE)

(73) Assignee: OSRAM GMBH, Munich (DE)

( * ) Notice: Subject to any disclaimer, the term of this patent is extended or adjusted under 35 U.S.C. 154(b) by 149 days.

(21) Appl. No.: 15/144,886

(22) Filed: May 3, 2016

(65) Prior Publication Data
US 2016/0327235 A1    Nov. 10, 2016

(30) Foreign Application Priority Data
May 4, 2015   (DE) .................. 10 2015 208 171

(51) Int. Cl.
*F21S 8/00*   (2006.01)
*F21V 5/00*   (2018.01)
(Continued)

(52) U.S. Cl.
CPC ............ *F21V 5/008* (2013.01); *A61B 1/0653* (2013.01); *F21S 41/14* (2018.01); *F21S 41/16* (2018.01);
(Continued)

(58) Field of Classification Search
CPC .......... F21V 5/008; F21V 5/004; F21V 5/007; A61B 1/0653; F21S 48/1145;
(Continued)

(56) References Cited

U.S. PATENT DOCUMENTS 5,270,859 A * 12/1993 Wirth ................... G02B 3/0056
                                                    359/419
7,106,529 B2 * 9/2006 Gurevich ............. G02B 3/0056
                                                    359/622

(Continued)

FOREIGN PATENT DOCUMENTS

| DE | 102007056402 A1 | 5/2009 |
| DE | 102013202334 A1 | 8/2014 |
| WO | 2014124814 A1 | 8/2014 |

OTHER PUBLICATIONS

German Search Report based on application No. 10 2015 208 171.0 (9 pages) dated Dec. 15, 2015 (for reference purpose only).

*Primary Examiner* — Karabi Guharay
*Assistant Examiner* — Meghan Ulanday
(74) *Attorney, Agent, or Firm* — Viering Jentschura & Partner MBB

(57) ABSTRACT

An irradiation apparatus includes a radiation unit for the emission of radiation in the form of a beam, a first microlens arrangement, downstream of the radiation unit, having a multiplicity of convergent microlenses, for dividing the beam into one partial beam per convergent microlens, and a convergent lens, downstream of the microlens arrangement, that overlays the partial beams, in an irradiated area. The microlenses have a first group and a second group. The microlenses in each group are identical, but the microlenses in the first group differ from the microlenses in the second group from their shape, size and/or focal length, so that a first region of the irradiated area, which is irradiated via the microlenses in the first group, differs from a second region of the irradiated area, which is irradiated by the microlenses in the second group, from its shape and/or its size.

16 Claims, 5 Drawing Sheets

(51) Int. Cl.
*G02B 3/00* (2006.01)
*G02B 27/09* (2006.01)
*A61B 1/06* (2006.01)
*G02B 19/00* (2006.01)
*F21S 41/14* (2018.01)
*F21S 41/26* (2018.01)
*F21S 41/265* (2018.01)
*F21S 41/16* (2018.01)
*F21W 131/406* (2006.01)
*F21K 9/64* (2016.01)
*F21Y 115/30* (2016.01)
*F21Y 105/10* (2016.01)

(52) U.S. Cl.
CPC ............. *F21S 41/26* (2018.01); *F21S 41/265* (2018.01); *F21V 5/004* (2013.01); *F21V 5/007* (2013.01); *G02B 3/0062* (2013.01); *G02B 19/0014* (2013.01); *G02B 19/0057* (2013.01); *G02B 27/0961* (2013.01); *F21K 9/64* (2016.08); *F21W 2131/406* (2013.01); *F21Y 2105/10* (2016.08); *F21Y 2115/30* (2016.08)

(58) Field of Classification Search
CPC ........................ F21S 48/1266; F21S 48/1275; G02B 3/0062; G02B 27/0961
USPC ......................................................... 362/268
See application file for complete search history.

(56) References Cited

U.S. PATENT DOCUMENTS

| 2002/0021497 | A1* | 2/2002 | McCulloch | B23K 26/073 |
| | | | | 359/622 |
| 2011/0188242 | A1 | 8/2011 | Brick et al. | |

* cited by examiner ured irradiated area regions;

IRRADIATION APPARATUS HAVING RADIATION UNIT

CROSS-REFERENCE TO RELATED APPLICATION

This application claims priority to German Patent Application Serial No. 10 2015 208 171.0, which was filed May 4, 2015, and is incorporated herein by reference in its entirety.

TECHNICAL FIELD

Various embodiments relate to an irradiation apparatus having a radiation unit for the emission of radiation in the form of a beam and a downstream optical system for beam shaping.

BACKGROUND

The radiation emitted by the irradiation apparatus may be in the UV or short-wave visible range, for example, and be used to irradiate a phosphor element, for example, which then emits conversion radiation, for example visible conversion light, in response to this excitation. The combination of an irradiation apparatus as a pump radiation source and a phosphor element arranged at an interval therefrom can be used to produce light sources having a high luminance that are able to be used in projection devices, for example. This is intended to illustrate one possible area of application for the irradiation apparatus according to the invention, but not to limit the generality of the subject matter.

SUMMARY

An irradiation apparatus includes a radiation unit for the emission of radiation in the form of a beam, a first microlens arrangement, downstream of the radiation unit, having a multiplicity of convergent microlenses, for dividing the beam into one partial beam per convergent microlens, and a convergent lens, downstream of the microlens arrangement, that overlays the partial beams, in an irradiated area. The microlenses have a first group and a second group. The microlenses in each group are identical, but the microlenses in the first group differ from the microlenses in the second group from their shape, size and/or focal length, so that a first region of the irradiated area, which is irradiated via the microlenses in the first group, differs from a second region of the irradiated area, which is irradiated by the microlenses in the second group, from its shape and/or its size.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

Figure 1:
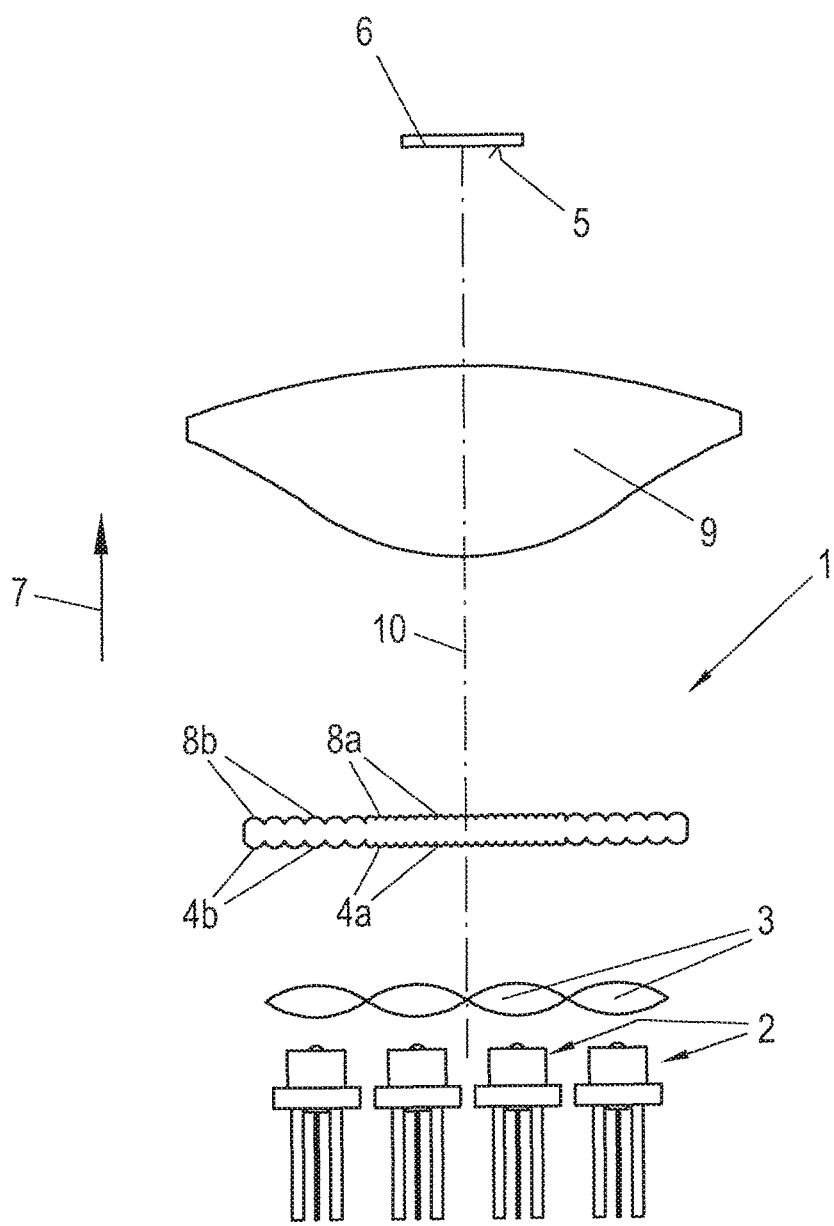
FIG. 1 shows a schematic, partially sectional, side view of an irradiation apparatus according to various embodiments.

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may be used herein to mean that the deposited material may be formed "indirectly on" the implied side or surface with one or more additional layers being arranged between the implied side or surface and the deposited material.

Various embodiments specify a particularly advantageous irradiation apparatus.

In various embodiments, an irradiation apparatus is provided having a radiation unit for the emission of radiation in the form of a beam in the time integral, a first microlens arrangement, downstream of the radiation unit, having a multiplicity of convergent microlenses, arranged next to one another in relation to the direction of radiation propagation, for dividing the beam into one partial beam per convergent microlens, and a convergent lens, downstream of the microlens arrangement, that overlays the partial beams, at least in the time integral, in an irradiated area, which convergent microlenses break down into at least a first group and a second group having a respective plurality of convergent microlenses. The irradiation apparatus may be set up for variable irradiation of the groups. The convergent microlenses in each group are identical, but the convergent microlenses in the first group differ from the convergent microlenses in the second group in at least one from their shape, size and focal length, so that a first region of the irradiated area, which region is irradiated via the convergent microlenses in the first group, differs from a second region of the irradiated area, which region is irradiated by the convergent microlenses in the second group, in at least one from its shape and its size.

Various embodiments are found in the dependent claims and also in the remainder of the disclosure, the depiction not always making a detailed distinction between apparatus and method or use aspects; the disclosure in respect of all of the claim categories can be read at least implicitly.

The irradiation apparatus according to various embodiments may allow variable irradiation of the irradiated area, for example by virtue of switching to and fro between beam guidance via the convergent microlenses in the first group (also just "first microlenses" below) and beam guidance via the convergent microlenses in the second group (also just "second microlenses" below). If a phosphor element, for example, is arranged in the irradiated area, then this thus allows different regions thereof to be exited, and the conversion light is then also emitted in correspondingly different regions (the emission region and the excitation region are each essentially congruent for a phosphor element).

An optical system (in the simplest case a convergent lens), for example, can be used to direct conversion light emitted in different regions (of the phosphor element) in different spatial directions, that is to say to convert the spatial distribution into an angle distribution. An area of application may be a motor vehicle headlamp, for example, in which the switching to and fro can correspond to changing between low beam and high beam.

In this case, the choice of irradiated area region is made by means of beam guidance using the relevant microlenses, which is used to homogenize the distribution of the irradiance over the respective irradiated area region at the same time. Thus, two functions are integrated, and the radiation guided by the microlenses in the same group is evenly distributed in the relevant irradiated area region. On the other hand, the irradiated area can also have its shape and/or size adjusted in the manner just described, however.

In various embodiments, a phosphor element is arranged in the irradiated area, that is to say that the irradiated area is situated approximately on a lateral area of the phosphor element. The aforementioned homogenization can then help to prevent local overheating and hence degradation of the phosphor element, for example. Down conversion is generally preferred, that is to say that the pump radiation is converted into radiation of longer wavelength, e.g. into visible light. However, it is also possible for a surface light modulator, for example a micromirror array or an LCD or LCOS imaging system, to be arranged in the irradiated area, for example; the homogenization can help to prevent damage in this case too.

In general terms, the "irradiated area" is obtained as a section through the rear focal plane of the convergent lens with all the partial beams. The rear focal plane of the convergent lens is situated on that side of the convergent lens that is averted from the first microlens arrangement (also just "microlens arrangement" below), that is to say downstream of said convergent lens in relation to the direction of radiation propagation. In general, "upstream/downstream" and "front/rear focal plane" relate to the direction of radiation propagation that the radiation has in each case along the path from the radiation unit to the irradiated area.

The shape of the first irradiated area region corresponds to the shape of the first microlenses, and that of the second irradiated area region corresponds to the shape of the second microlenses, when the microlenses have the same orientation and the respective partial beams are overlaid congruently (see below in detail). In the case of circular microlenses, for example, the corresponding irradiated area region is thus likewise circular, whereas in a preferred case of rectangular microlenses, it is likewise rectangular. The microlenses can have a round, in particular circular, or polygonal shape, for example, as seen in the direction of radiation propagation, for example may be rectangular, e.g. square, or even hexagonal, for example.

In addition, the size and focal length of the first/second microlenses determine the size of the first/second irradiated area region, with the irradiated area region increasing with the size of the microlenses and decreasing with the focal length thereof (which becomes longer). The smaller a microlens/longer the focal length thereof, the smaller the divergence of the partial beam, which means that the irradiated area region likewise becomes smaller (cf. FIG. 3 for the purposes of illustration with associated description). The "size" of a microlens is the opening width thereof; by way of example consideration is given to the area content of a vertical projection of the microlens into a plane perpendicular to the optical axis of said microlens (and compared as a "size" with the corresponding value from another microlens). "The same shape" means shapes that can be transferred to one another by means of translational displacement and/or rotation and/or scaling, for example.

The microlenses now "break down" into at least two groups, that is to say can be classified accordingly, that is to say associated with a respective group. The association with the group generally has no implication with regard to the spatial distribution of the microlenses in the microlens arrangement. The microlenses in a group thus do not necessarily have to be provided in direct proximity to one another, even though this may be provided for variable radiation that is as simple to implement as possible.

Each group has a plurality of identical microlenses provided, for example at least 10, 20, 30, 40, 50, 60, 70, 80, 90 or 100 microlenses with increasing preference in this order; possible upper limits are no more than 2000, 1500, 1000, 500 and 250, for example. The microlens arrangement can also have, in addition to the microlenses in the first and second groups, further microlenses, generally even microlenses that differ from one another in shape and/or size and/or focal length. In various embodiments, the further microlenses are also associated with a respective group, however, that is to say that each microlens is associated with a group containing identical microlenses. There are at least two groups and preferably no more than 20, 15, 10 or 8 groups (with increasing preference in the order cited). The lower limits may be at least 2, 3, 4, 5 groups, for example.

The size and shape of a respective (first/second/further) irradiated area region are determined according to the irradiance distribution for irradiation via the respective microlenses. In this case, the edge of a respective irradiance distribution is by definition intended to be where the irradiance has fallen to half the mean irradiance (which is achieved via the respective microlenses); this definition is preferred, and in general the edge could also be where the irradiance has fallen to 1/e of the mean irradiance, for example.

The beam emitted by the radiation unit is considered in the time integral because the irradiation apparatus is set up for selective irradiation of the first/second microlenses. The beam is thus obtained as the union of a first beam, passing through the first microlenses, and a second beam, which passes through the second microlenses, and, if present, of further beams from further microlenses. The microlens arrangement can, by way of example, also be scanned, for example using a laser scan method, in which case the beam is obtained in integrated form over the entire raster field.

The variable irradiation for which the irradiation apparatus may be set up can, by way of example, be achieved electronically by virtue of individual sources being connected or disconnected and/or mechanically by virtue of optical elements being moved, for example by tilting a mirror to alter the beam deflection or displacing a lens to alter the beam flare (see below in detail). It is also possible for the microlens arrangement to be moved relative to the radiation unit (and the remainder of the components of the radiation apparatus), for example to have a periodic oscillation (vibration) applied.

In general, "variable irradiation" means that at least the ratio of the radiation power guided via the first microlenses to the radiation power guided by the second microlenses can be altered, and e.g. the irradiation of at least one of the groups can be disconnected completely during operation of the irradiation apparatus, and, for example, the irradiation is individually connectable and disconnectable for each of the groups. A variable irradiation is not obligatory, however, the reason being that a pattern resulting from different irradiated area regions being overlaid may be of interest even just statically.

The partial beams are "overlaid", at least in the time integral, in the irradiated area in accordance with the variable irradiation, that is to say that they all have a common intersection in the irradiated area, and e.g., the regions of the irradiated area that are irradiated in each group by the partial beams are congruent and hence congruent with the respective irradiated area region. In various embodiments, the overlay in each group is also already obtained at one instant (not just in the time integral), that is to say not scanned, for example.

In various embodiments, the area focal points of the first and second irradiation area regions coincide, specifically at the point at which the optical axis of the convergent lens passes through the irradiated area.

The microlens arrangement "divides" the beam into the partial beams that, immediately downstream of the microlenses, are each convergent and, as a result, actually physically separated from one another, for example in the rear focal plane of the microlens arrangement; downstream of the rear focal plane, an overlap in the partial beams is then again possible.

In general, the term "lens" relates, within the context of this disclosure, to a transparent body having at least one curved refractive face, which is preferably an outer face of the body; the opposite outer face may generally also be planar, for example. The curved refractive face of a microlens may be parabolic; the refractive face of the downstream convergent lens may be aspherical.

The convergent lens may generally also be a lens system, for example, that is constructed from a plurality of single lenses (which are arranged in succession). In various embodiments, however, the convergent lens is a single lens in which the light entry and light exit faces may be curved.

The lenses of the microlens arrangement are arranged "next to one another", that is to say connected in parallel to a certain extent, in relation to the direction of beam propagation; this means that radiation that has traveled through a microlens passes through no other microlens in a reflection-free manner, that is to say particularly apart from backscatter and the like. In various embodiments, the microlenses lie in a common plane (in each case with the apex at the respective refractive face) on which the optical axis of the convergent lens/the optical axes of the microlenses are perpendicular.

In the present case, the optical axis under consideration for a rotationally symmetrical lens is that axis about which there is the symmetry. In various embodiments, the microlenses of the microlens arrangement each have an optical axis, and with further preference, these optical axes are parallel to one another. In various embodiments, the convergent lens has an optical axis, and for example, the optical axis of the convergent lens is parallel to the (mutually parallel) optical axes of the microlens arrangement.

The radiation strikes the microlens arrangement preferably in collimated form. Generally, the radiation may be laser radiation, that is to say that the radiation unit is a laser unit. The radiation unit may be constructed from a plurality of radiation sources, for example at least 2, 3, 4, 5, 6, 7, 8, 9 or 10 radiation sources, possible upper limits being no more than 1000, 800, 600, 400, 200, 100 and 50, for example. The radiation sources can (at least in groups) emit radiation of different dominant wavelength, and may emit radiation of the same wavelength, and, for example, they are of identical design.

The radiation source provided may also be a light emitting diode (LED), for example, a laser diode being preferred as the radiation source. In various embodiments, a plurality of laser diodes arranged in an array form the radiation unit. In various embodiments, it is then possible for one collimated laser beam per laser diode to strike the microlens arrangement, the laser beams being incident parallel to one another.

This example illustrates that the "beam" does not necessarily have to be coherent (despite the integration with respect to time), but rather may even be split into subbeams upstream of the microlens arrangement. In each group, a plurality of subbeams (laser beams) can then strike the microlens arrangement, cf. FIG. 2 for the purposes of illustration. A subbeam may be intended to strike at least 5, 10 or 15 microlenses (with increasing preference in the order of citation); possible upper limits may be no more than 200, 150 or 100 microlenses, for example. In each group, at least 20, 40 or 50 microlenses may be intended to be irradiated (with increasing preference in the order of citation); possible upper limits may be no more than 2500, 1250 or 500 microlenses, for example. Overall, the beam may be intended to irradiate at least 40, 80 or 100 microlenses (with increasing preference in the order of citation); possible upper limits may be no more than 5000, 2500 or 1000 microlenses, for example.

In various embodiments, the microlenses in at least one of the groups have the same orientation, this may apply for the microlenses in all of the groups in each case (that is to say that the microlenses in each group have the same orientation in relation to one another). "The same orientation" means that they can be aligned solely by means of translational displacement. The regions of the irradiated area that are irradiated via the microlenses having the same orientation (and in the same group) are congruent and each correspond to the respective irradiated area region (see above).

In various embodiments, the microlenses in at least one of the groups, e.g. in the first and second groups, e.g. in all of the groups, have a rectangular shape. This relates to a plan view, that is to say a view along the optical axis of the respective microlens. The lateral edges of a respective rectangle are preferably in a ratio (of shorter lateral edge to longer lateral edge) of at least 1:10, with increasing preference in this order at least 1:8, 1:6, 1:4, 1:2 or 2:3, and, for example, may be square microlenses.

In various embodiments, the first and second microlenses differ (at least) in their size, with the small microlenses and the large ones being in a size ratio of at least 1:100, 1:80, 1:60, 1:40, 1:20 or 1:10, with increasing preference in this order. Upper limits may be no more than 9:10, 4:5, 7:10, 3:5 or 1:2, for example, with increasing preference in this order. The provision of an upper limit may expressly also be of interest independently of the provision of a lower limit (and vice versa) and is also intended to be disclosed in this form.

In various embodiments, the first and second microlenses differ exclusively in their size, that is to say that they have the same shape. If present, the microlenses in a further/in further group(s) then also have the same shape. A possible shape is simply a rectangular shape.

In various embodiments, the microlenses in at least one of the groups are parabolic, which in this context relates to the curvature of the refractive light passage face of the lens. In various embodiments, the first and second (and if present, also further) microlenses are parabolic, specifically, with further preference, with the same radius of curvature. If the first and second microlenses then differ in their size, for example, the arrow height (height of the spherical segment) for the larger microlenses is greater than for the smaller ones. The provision of parabolic microlenses can advantageously help to reduce complexity for the design of a microlens arrangement.

In various embodiments, the first microlenses are arranged in a first segment and the second microlenses are arranged in a second segment, the first segment being surrounded by the second segment, that is to say that the second microlenses extend around the first ones in the manner of a frame. This again relates to a plan view, looking onto the microlens arrangement along the optical axes of the microlenses. In respect of the directions perpendicular to these optical axes, the first segment is surrounded by the second segment; that is to say that there is meant to be, outwardly from each first microlens in each of the directions perpendicular to the optical axis thereof, at least one second microlens, normally several in each case (per direction perpendicular to the optical axis).

In various embodiments, the microlenses whose irradiated area region is smaller, that is to say that are smaller and/or have a greater focal length, are arranged centrally. The reason is that since the irradiated area region is smaller, the radiation power to be guided via the relevant microlenses will normally also be lower. Accordingly, the outer microlenses may have more associated radiation sources than the inner ones, for example. If the radiation sources are arranged in an array, for example, then the radiation sources associated with the outer microlenses can be distributed better around the few radiation sources associated with the inner microlenses than vice versa.

In the case of a further/of further group(s), the microlenses thereof may also (each) be arranged in a segment, the segments then particularly preferably being interleaved. A third segment thus then surrounds the first two and (if present) a fourth surrounds the first three, and so on.

In general, "microlens arrangement" can, in various embodiments, relate to microlenses with a defined relative position in relation to one another, and for example, the microlens arrangement is in one piece, that is to say that the microlenses cannot be separated from one another without destroying them (for example are adhesively bonded to one another). In various embodiments, the microlens arrangement is monolithic, that is to say is formed from a material without restriction by material boundaries inside. In principle, an appropriate microlens arrangement can also be formed by material removal (for example by grinding); in respect of mass production too, manufacture by casting in a mold may be provided, however, that is to say that the microlens arrangement is an injection molded part, for example.

The microlens arrangement is not necessarily in one piece/monolithic, however, but rather a microlens arrangement in which the first microlenses are mounted so as to be mobile relative to the second ones (and accordingly the second ones relative to the first ones) may also be of interest. In each group, the microlenses in this arrangement may have a defined relative position in relation to one another, that is to say that the microlens arrangement may then be provided from multiple (an amount corresponding to the number of groups) parts having multiple pieces in relation to one another, each part then having the respective microlenses in a group and e.g. itself being in one piece/monolithic in the aforementioned sense.

In conjunction with the "second microlenses surround first microlenses" variant just described, it is possible for the first group to be held rotatably in the second, for example. However, the groups may even be displaceable relative to one another with a direction of movement perpendicular to the (mutually parallel) optical axes of the microlenses, for example. A possible area of application for the irradiation apparatus with microlenses that are mobile relative to one another (in groups) may be in the field of effect lighting, for example.

Likewise in this respect, inter alia, movement of the microlens arrangement overall relative to the remainder of the irradiation apparatus, for example, may also be of interest, for example rotation, e.g. about an axis of rotation that is parallel to the optical axes of the microlenses, displacement and/or vibration, that is to say periodic movement.

Generally, the microlenses may be mobile relative to one another, that is to say not only in groups, perpendicular to the (mutually parallel) optical axes of the microlenses. The microlens arrangement can, to a certain extent, be fanned out, that is to say that the intervals between the microlenses can be enlarged. By way of example, it is thus possible to change the number of microlenses being irradiated by moving some microlenses out of the region that is irradiated by fanning them out. To this end, the microlenses may, by way of example, be embedded in a flexible and accordingly deformable matrix material, for example as single lenses between which at least optically functional cavities (without microlenses) are then obtained. As described at the outset, variable irradiation of the irradiated area, for example when a phosphor element is arranged therein, can produce a radiation pattern with varying spatial distribution, which radiation pattern can be converted into an angle distribution using an optical system. The relative movement of the microlenses can thus be used to produce an excitation pattern that can be used for effect lighting that varies in different spatial directions.

Generally, an irradiation apparatus having such a microlens arrangement with microlenses that are mobile relative to one another (in groups) could even be of interest when the irradiance striking the respective group is constant during operation. Only the movement within the microlens arrangement can produce varying irradiation.

In various embodiments, however, the irradiation apparatus is set up such that the ratio of the first irradiance (which strikes the first microlenses) to the second irradiance (which strikes the second microlenses) can be altered during operation of the irradiation apparatus. In various embodiments, the irradiation of at least one of the groups can be completely disconnected (and also reconnected) during operation. The ratio of the first to the second irradiance is considered on average over time in this case. The reason is that the irradiance can also be set by means of pulse width modulation, for example; the average over time is taken over the smallest possible period in each case.

The radiation unit can have a first radiation source, at least the greater part of whose radiation irradiates the first microlenses, and a second radiation source, at least the greater part of whose radiation irradiates the second microlenses (preferably, exclusively the first or second microlenses are irradiated in each case). The irradiation apparatus may then be set up such that a change in the radiation power of the first radiation source, if need be with a linear or nonlinear proportionality constant ($m \neq 1$) that is different from 1, results in a change in the radiation power of the second radiation source, may be independent thereof.

In various embodiments, the irradiance ratio can thus be achieved by means of the average output power of the individual radiation sources in the case of a radiation unit constructed from multiple radiation sources. For example in the case of an array of laser diodes that each emit separately collimated laser radiation in mutually parallel subbeams, variation of the irradiance ratio can occur even with an unaltered beam angle (of 0°, for example).

On the other hand, the irradiation apparatus may also be set up such that the beam angle that is obtained from the volume filled by the radiation immediately upstream of the microlens arrangement can be altered. The union of the volumes filled by the radiation corresponds to the beam, that is to say that the volumes are subsets of the latter. The volume and hence the beam angle are proportioned according to the half-value width. The beam angle can vary at least in relation to a sectional plane passing through the microlens arrangement parallel to the optical axes of the microlenses, e.g. in respect of all sectional planes (for example in the case of a cone, which can be flared and constricted).

In the case of a small beam angle, it is possible, for example with interleaved groups (see above in detail), for only the inner microlenses to be irradiated, and the flared radiation can then strike both the first and the second microlenses.

The "phosphor element", which has already been mentioned several times, may be a static phosphor element, for example a phosphor lamina. On the other hand, the phosphor element may also move, however, for example about an axis of rotation, for example as a phosphor roller or preferably as a phosphor wheel. The axis of rotation may then at rest relative to the remainder of the irradiation apparatus.

In various embodiments, the irradiation apparatus additionally has a second microlens arrangement that is likewise constructed from a multiplicity of microlenses arranged next to one another. These are meant to correspond to the microlenses in the first microlens arrangement in terms of their size, shape and relative arrangement in relation to one another (within the respective microlens arrangement), e.g. also in terms of their focal length (see below in detail), and, based on the direction of radiation propagation, to be arranged between said first microlens arrangement and the convergent lens. In this case, the microlenses in the first and second microlens arrangements are meant to "interact in respective pairs", that is to say that each partial beam (which by definition is associated with precisely one microlens in the first microlens arrangement) is meant to pass through precisely one microlens in the second microlens arrangement. Two accordingly interacting microlenses in the first and second microlens arrangements are referred to as a "microlens pair".

In each microlens pair, it may be provided for the rear microlens to be arranged in the rear focal plane of the front microlens and/or for the front microlens to be arranged in the front focal plane of the rear microlens, and for example, both are true. Insofar as statements are made in relation to a microlens pair, this then may apply to at least all microlenses in a group, e.g. to all microlenses that can be associated with a group, and e.g. to all microlenses in the two arrangements. The effect of two series-connected microlens arrangements (also "dual microlens arrangements" below) may lie in increased tolerance toward radiation with tilted incidence, for example. At least within certain limits, radiation with tilted incidence can thus nevertheless still be overlaid congruently in the irradiated area (insofar as the microlenses are identical).

For example in the case of collimated laser radiation (for example multiple laser beams that are each separately collimated), a maximum tilt of no more than 3° may be provided in the case of a single microlens arrangement, no more than 2° being a further preference and no more than 1° being possible (the tilt is taken relative to the mutually parallel optical axes of the microlenses). Although, even in the case of a dual microlens arrangement, collimated radiation that is incident parallel to the optical axes may be provided, tolerance toward tilting is increased; by way of example, the latter is meant to be no more than 15°, with increasing preference in this order no more than 13°, 11°, 10°, 9°, 8°, 6° or 5°.

In relation to the microlens pairs again: it may be provided for the microlens pairs in the different groups to have the same length. The length of a microlens pair is taken from the entry face of the microlens in the first arrangement to the exit face of the microlens in the second arrangement. If the microlens pairs have the same length, then this can, by way of example, simplify manufacture, for example demolding of an injection molded part.

On the other hand, microlens pairs of different length may also be of interest, that is to say for example microlens pairs that have the same length in each group but a different length in comparison with the groups. In conjunction with the aforementioned requirement that, in each microlens pair, the rear focal plane of the front microlens coincides with the rear microlens and the front focal plane thereof coincides with the front microlens, the microlens pairs of different length then also have a different focal length.

In other words, microlens pairs of different length allow the focal length of the microlens pairs in a respective group to be chosen such that the irradiated area region is provided with the desired size. In order to produce an irradiated area region that is as small as possible, for example, the size of the microlenses can admittedly be chosen to be small, but a certain minimum size may be necessary for production-related reasons, for example. So as then to reduce the irradiated area region further, the focal length can be increased. Otherwise, this also applies to an irradiation apparatus having just a first microlens arrangement. If a second microlens arrangement is provided, then, so that the preferred focal plane condition can still be satisfied, the length of the microlens pairs having a longer focal length may be increased accordingly.

Generally, the details found above for the first microlens arrangement are also meant to be disclosed for the second microlens arrangement, which relates particularly to the possible arrangement of the microlenses in one plane and to the possible one-piece/monolithic embodiment of said arrangement. The first and second microlens arrangements may have multiple pieces in relation to one another and then preferably be spaced apart by means of an air gap. By way of example, a planar exit face of the first microlens arrangement, which is situated opposite the curved entry face thereof, may be facing opposite a planar entry face of the second microlens arrangement (spaced apart by means of the air gap), which planar entry face of the second microlens arrangement is situated opposite the curved light exit face thereof.

The first and second microlens arrangements may also be provided integrally with one another, however, e.g. monolithically, for example as an injection molded part. The microlenses in the first microlens arrangement are then shaped as a curved surface on the entry side of this monolithic part, and the microlenses in the second microlens arrangement on the exit side.

In various embodiments, the rear focal planes of the microlenses lie in a common plane and this "rear focal plane" of the microlens arrangement coincides with the front focal plane of the convergent lens. Downstream of the convergent lens, the partial beams are then each separately collimated. In the case of the dual microlens arrangement, the refractive faces of the second microlens arrangement that face the convergent lens then preferably lie in this plane, and ideally they thus each have their apex at a tangent to the plane.

In various embodiments, which relates e.g. to a simple microlens arrangement, the first microlens arrangement is provided on the entry side of a basic body, that is to say is formed in the entry face thereof. Each of the microlenses has a focus, and it is preferably intended to be situated outside the basic body, as a further preference outside transparent optical elements in general, that is to say also outside the convergent lens. The focuses of the individual microlenses are then preferably between the exit face of the basic body and the convergent lens. Appropriate focusing can prevent excessive input of power into the basic body or the convergent lens and hence overheating, for example.

As already mentioned at the outset, the embodiments also relate to a method for operating an irradiation apparatus as disclosed in the present case. In this case, the first group of microlenses is irradiated at a first irradiance and the second group is irradiated at a second irradiance, the ratio of the first and second irradiance being varied in order to accordingly vary the irradiance in the respective irradiated area regions.

In this case, the first and/or second irradiance can also become equal to zero, that is to say can also be switched to and fro between irradiation of the first and second microlenses, for example. On the other hand, there may also be provided, by way of example, for one group to be permanently irradiated and the other to be connected as required; the irradiance of the microlenses of the permanently irradiated group can also be adjusted in this case, for example decreased when the other group is connected, so that the irradiance is kept constant overall, for example.

Various embodiments also relate to the use of an irradiation apparatus as disclosed in the present case for motor vehicle exterior lighting, particularly for variable illumination of the road with a headlamp. Possible areas of application may also be in the field of effect lighting; on the other hand, the irradiation apparatus can also be used for operating area lighting, for which variably adjustable irradiation may also be of interest. The irradiation apparatus can additionally be used as a light source for a projection device, endoscope or stage spotlight, for example for lighting scenes in the film, television or theater field.

FIG. 1 shows a schematic side view of an irradiation apparatus 1 according to various embodiments. The irradiation apparatus 1 has a plurality of laser diodes 2 (in the present case 16 laser diodes) as a radiation unit, the beam propagation not being shown in FIG. 1 for the sake of clarity, and, in this respect, reference being made to the following figures.

A respective laser beam emitted by one of the laser diodes 2 is separately collimated using a respective collimation lens 3. Downstream of the collimation lenses 3, the laser beams then strike a microlens arrangement 4, which is shown in section. The microlenses 4 in said microlens arrangement can be divided into a first group having small microlenses 4a and a second group having larger microlenses 4b. In each group, the microlenses 4 are identical to one another, that is to say that they have the same focal length (the same radius of curvature), the same size and the same shape.

As is then explained in more detail with reference to FIG. 2, the differently sized first 4a and second 4b microlenses can then be used to irradiate differently sized regions of an irradiated area 5. In the irradiated area 5, as shown in FIG. 1, a phosphor element 6 is arranged (not shown in FIG. 2) in the present case, and the radiation emitted by the laser diodes 2 is thus used as pump radiation to excite the phosphor element 6. When different regions of the phosphor element 6 are excited, the conversion light emitted thereby in response to this excitation is also emitted from different regions.

The phosphor element 6 can be operated in transmission, for example, and it is then possible for an imaging optical system (not shown) to be provided downstream of the phosphor element 6 in relation to a direction of propagation 7 of the radiation, which optical system converts the spatial distribution (of the conversion light emission) into an angle distribution. The conversion light emitted at different locations is thus deflected in different spatial directions.

The first microlens arrangement 4 guides the radiation via a second microlens arrangement 8, the microlenses 8 in the second arrangement being provided to correspond in respective pairs to the microlenses 4 in the first arrangement in terms of size, shape and focal length. The microlenses 4, 8 are arranged such that each microlens 4 in the first arrangement forms a functional pair with precisely one microlens 8 in the second arrangement. The microlenses 4 in the first arrangement break down a beam striking the microlens arrangement 4 into partial beams, in which case each of the partial beams passes through precisely one microlens in the second microlens arrangement 8 (namely the one in the respective functional pair). The beam is the sum total of all the laser beams.

A convergent lens 9 downstream of the second microlens arrangement 8 overlays the partial beams in the irradiated area 5; the irradiated area 5 lies in the rear focal plane of the convergent lens 9.

Figure 2A:
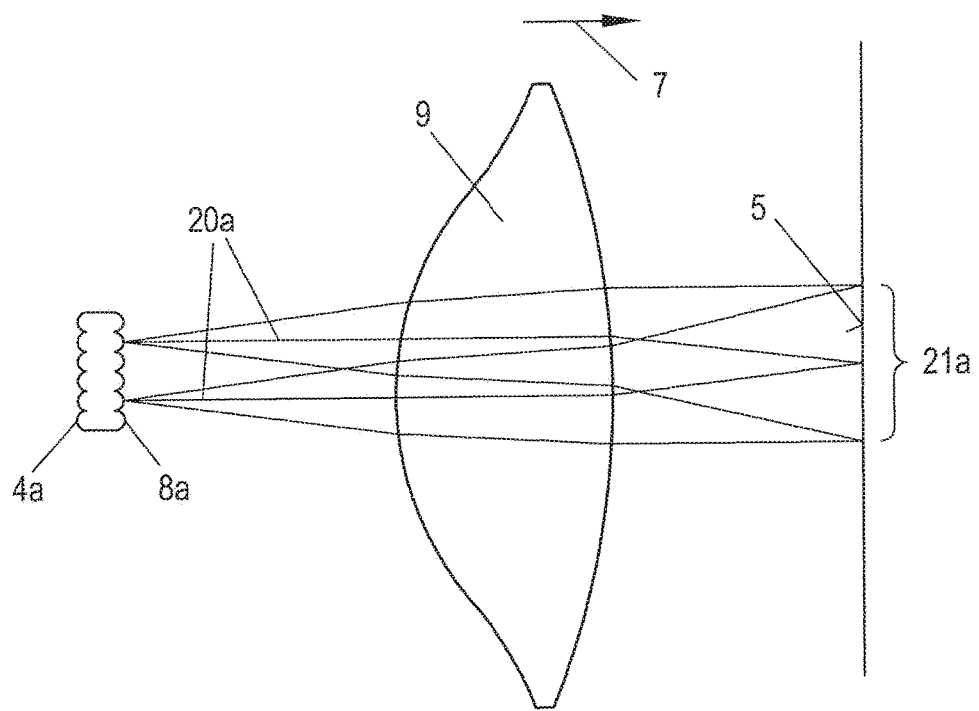
FIGS. 2A and 2B show schematic side views with microlenses of different size to illustrate the accordingly differently sized irradiated area regions.
Figure 2B:
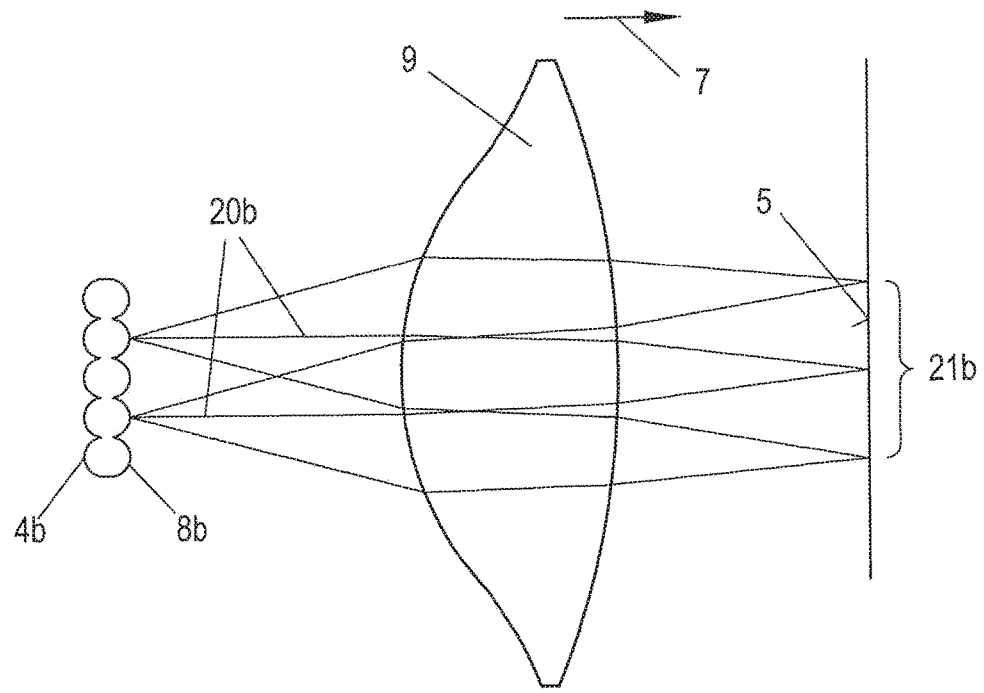

FIG. 2a and FIG. 2b illustrate such partial beams 20a, b for the smaller microlenses 4a, 8a (FIG. 2a) and for the larger microlenses 4b, 8b (FIG. 2b). For the sake of clarity, only the partial beams 20a, b from two of the microlenses 4a, 8a, 4b, 8b, a plurality of which are provided in reality, are shown in each case. Since this design relates to two microlens arrangements 4, 8 having microlenses that functionally interact in pairs, the text below refers to a respective partial beam 20a, b for a respective microlens pair 4, 8 and to the size/shape/focal length of the microlens pair 4, 8.

In a respective subregion 21a, b of the irradiated area 5, the respective partial beams 20a, b are overlaid congruently. In each group, each of the microlenses pairs 4, 8 thus irradiates the entire respective irradiated area region 21a, b in each case. In conjunction with the overlay, uniform irradiation is achieved.

In the present case, the microlens pairs 4, 8 are arranged in the front focal plane of the convergent lens 9 and the partial beams 20a, b are each collimated separately. Thus, partial beams 20a, b that are each collimated separately and tilted in relation to one another are overlaid in the irradiated area 5.

Generally, the arrangement in the microlens pairs 4, 8 in the front focal plane of the convergent lens 9 is not obligatory, however, and the respective partial beams 20a, b from the microlens pairs 4, 8 in a respective group would also be overlaid congruently in the irradiated area 5 if the microlens pairs 4, 8 were in an offset position in relation to the front focal plane of the convergent lens 9. If they were to move closer to the convergent lens 9, the partial beams 20a, b would be divergent downstream of the convergent lens 9; on the other hand, they would be convergent if the microlens pairs 4, 8 were situated outside the front focal length of the convergent lens 9.

Depending on whether irradiation occurs via the microlens pairs 4a, 8a in the first group (FIG. 2a) or via the microlens pairs 4b, 8b in the second group (FIG. 2b), the irradiated area region 21a, b is smaller or larger. The choice of irradiated microlens pairs 4, 8 can thus be used to adjust the size of the irradiated area, only two groups of microlens pairs 4, 8 of different size being shown in the present case for the sake of clarity, but there may also be many more than two groups in practice.

Figure 3:
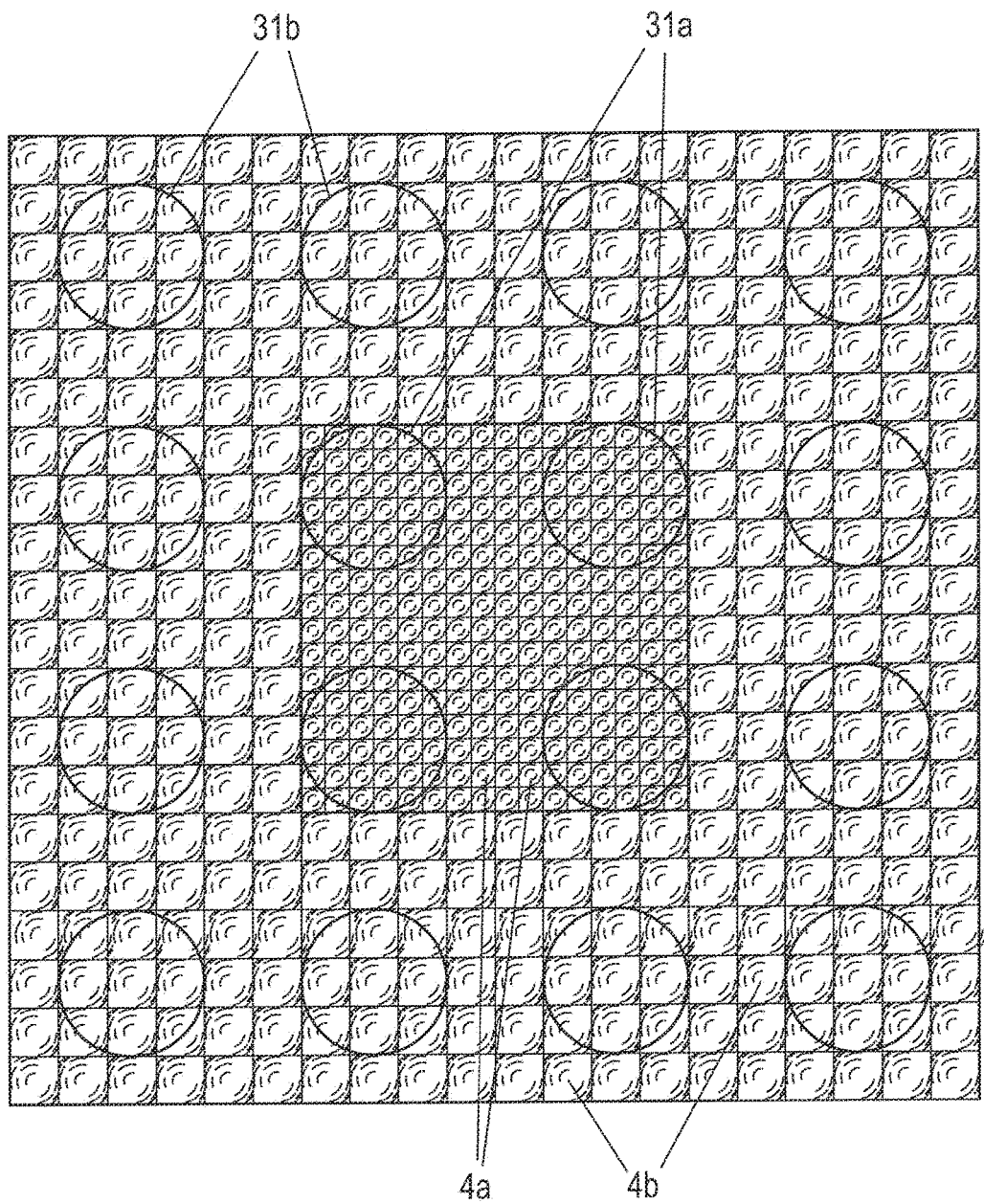
FIG. 3 shows a plan view of a microlens arrangement in an irradiation apparatus according to various embodiments with multiple schematically shown laser spots.

FIG. 3 shows a plan view of the microlens arrangement 4, looking along the direction of propagation 7 of the laser radiation. The microlenses 4a, b of different size can be identified therein. In addition, essentially circular irradiated regions 31 are denoted that each mark the region of the microlens arrangement 4 that is irradiated by a respective laser diode 2. The laser beams emitted by each of the laser diodes 2 are each separately collimated, parallel to one another and flare perpendicular to a common arrangement area of the laser diodes 2 (the laser diodes 2 are mounted in the planar arrangement area). The arrangement of the irradiated regions 31 corresponds to the arrangement of the laser diodes 2.

Each of the laser diodes 2 is associated with precisely one group of the microlenses 4 (the microlens pairs 4, 8), and thus irradiates exclusively microlenses 4 of the same size. The inner four laser diodes 2 irradiate the small, first microlenses 4a, whereas the twelve outer laser diodes 2 irradiate the second, larger microlenses 4b.

Control/driver electronics can now be provided such that they cater for the outer 16 laser diodes 2 as one group and for the inner four laser diodes 2 as another group. The output power from the laser diodes in one group can be set independently of that from the laser diodes in the other group, but within a group, the output power is the same from laser diode 2 to laser diode 2.

In a first operating state, merely the four inner laser diodes 2 can be operated and accordingly the small microlenses 4a can be irradiated, for example. Accordingly, the first, small irradiated area region 21a of the irradiated area 5 is irradiated, that is to say a small subregion of the phosphor element is excited. If exclusively the twelve outer laser diodes 2, for example, are operated in another operating state, then accordingly the second microlenses 4b are irradiated and hence the correspondingly large irradiated area region 21b of the irradiated area 5 is irradiated.

As an alternative to the arrangement shown in FIG. 3, it would be possible, in the case of a further group or of further groups of microlenses, for the outer region, which is catered for by the twelve laser diodes, to be broken down further, for example into rectangles that are obtained by extending the lateral edges of the central rectangle (not shown). The rectangles above and below and to the left and right of the central rectangle would then be catered for by two laser diodes 2 each, and the rectangles at the corners by one laser diode 2 each.

The second microlenses 4b and the further group(s) can then be distributed over the rectangles according to the power requirement, rectangles having microlenses 4 in the same group not needing to border one another.

An effect of the provision of microlens pairs 4, 8, that is to say in the second microlens arrangement 8, can consist in a certain tolerance for radiation with tilted incidence, for example. The optical axes of the microlens pairs 4, 8 are parallel to the optical axis 10 of the convergent lens 9, but are not shown in detail for the sake of clarity (cf. FIG. 1 for illustration). Ideally, the laser beams from the laser diodes 2 are parallel to the optical axes of the microlens pairs 4, 8. If tilting occurs, for example through production, then the respective partial beams 21a, b from a respective group can nevertheless be congruently overlaid provided that the tilt does not exceed an acceptance angle for the microlens pairs 4, 8.

Within the acceptance angle range, the microlens 4a, b in the first arrangement focuses on that microlens 8a, b in the second arrangement that is part of the respective microlens pair 4, 8. Outside the acceptance angle range, the radiation (also) strikes other microlenses 8, and ghost images can arise.

Generally, the provision of microlens pairs 4, 8 is not obligatory, however. In the case of radiation that is incident parallel (to the optical axes of the microlenses 4a, b), for example, a single microlens arrangement 4 can also overlay the respective partial beams 20a, b from each group congruently in the irradiated area 5 (together with the convergent lens 9).

Figure 4:
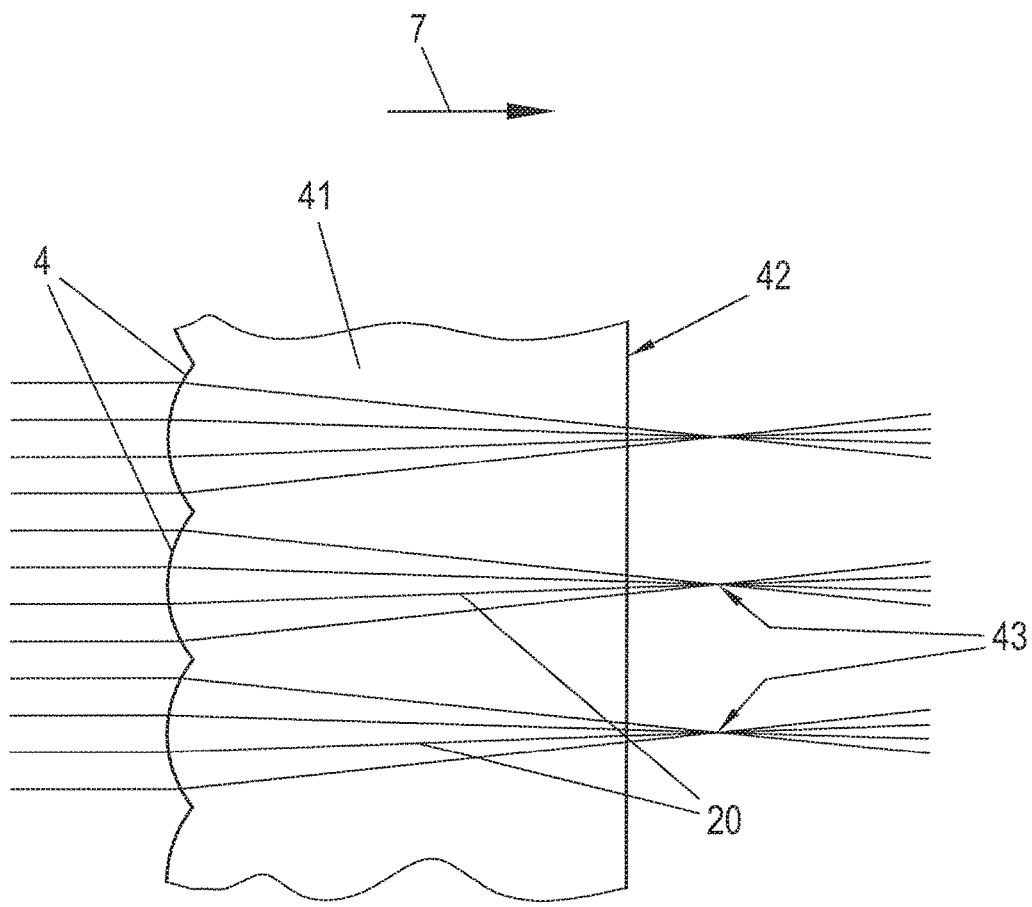
FIG. 4 shows a beam guidance in the case of a simple microlens arrangement.

FIG. 4 shows a schematic section through a simple microlens arrangement 4 of this kind. The microlenses 4a, b are formed on the entry side of a basic body 41. The exit side 42 thereof, which is opposite the microlenses 4a, b, is planar. The downstream convergent lens and the phosphor element are not shown for the sake of clarity, and in this respect, reference is made to the design shown in FIG. 1 and FIG. 2 and to the associated description.

The length, taken in the direction of radiation propagation 7, of the basic body 41 is now chosen such that the focuses 43 are outside the basic body 41, that is to say that the partial beams 20 are focused downstream of the basic body 41. This makes it possible to prevent excessive input into the basic body 41, for example.

FIG. 2 illustrates what influence the size of the microlenses 4a, b or microlens pairs 4, 8 has on the size of the irradiated region 21a, b of the irradiated area 5. The larger the microlenses 4a, b, the greater the divergence, and accordingly the larger the irradiated region.

However, as an alternative to or in combination with setting by means of the size, it is also possible for the size of the respective irradiated area region 21a, b to be set by means of the focal length. The shorter the focal length of the microlenses 4a, b, the greater the divergence and accordingly the larger the irradiated area region 21a, b.

Figure 5:
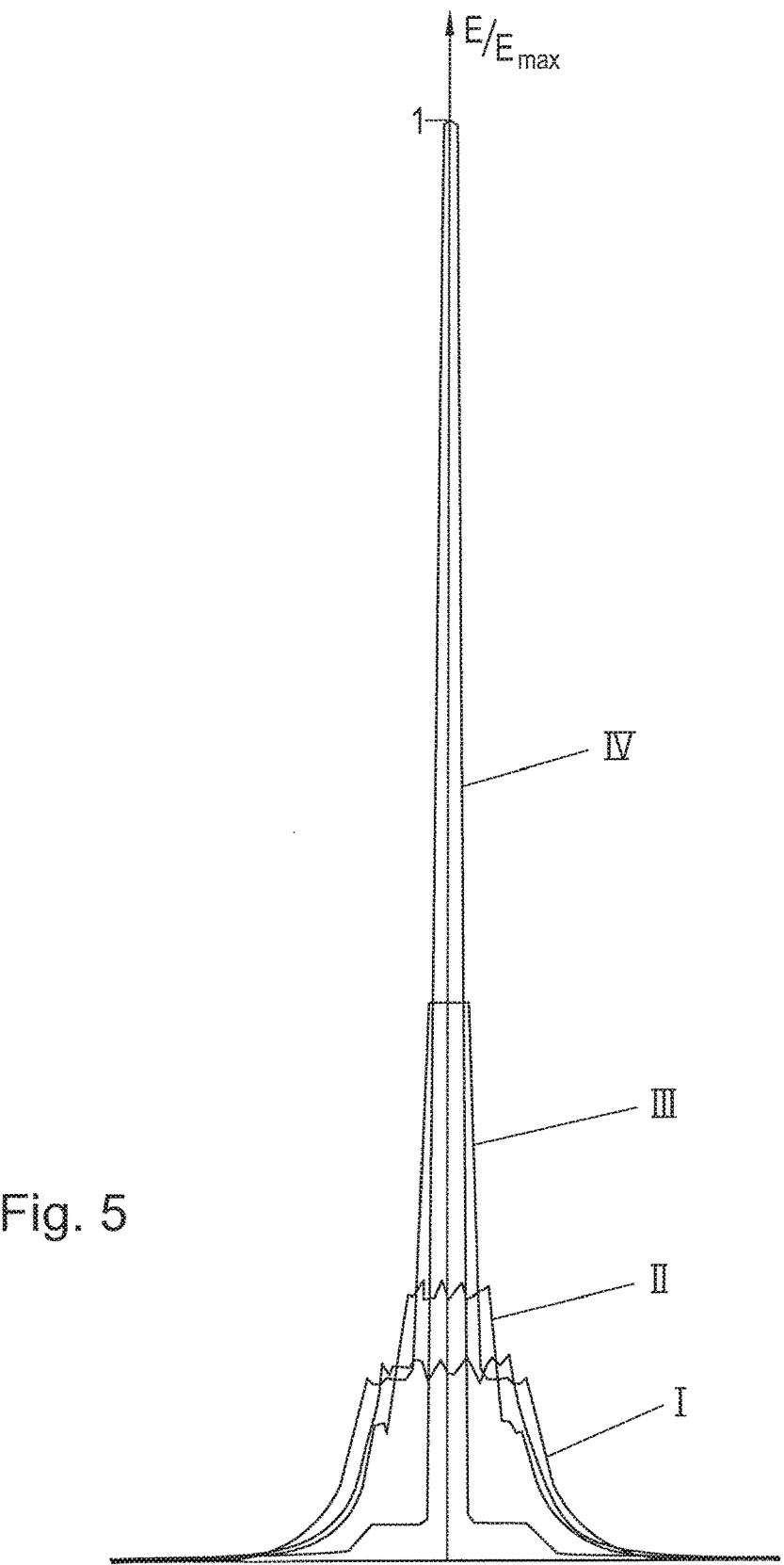
FIG. 5 shows a graph to illustrate the irradiance profile in the irradiated area on the basis of the focal length.

FIG. 5 illustrates the profile of the irradiance in the irradiated area (based on results from ray tracing simulations, performed on a simple microlens arrangement). The microlenses (including in the two groups in relation to one another) have the same size and, in a reference case (graph I), also the same focal length.

The three further graphs II-IV then illustrate how the irradiance profile changes when the focal length of the first, inner microlenses 4a is altered (the groups are arranged in a manner comparable to FIG. 3). As focal length increases, the divergence of the partial beams 20a passing through the first microlenses 4a decreases. Accordingly, that region 21a of the irradiated area 5 that is irradiated via the first microlenses 4a becomes smaller. A plateau forms in the center of the irradiated area 5, the width of said plateau—taken along the irradiated area 5—decreases as focal length increases. The radiation power guided via the first microlenses 4a is kept constant in this case, for which reason the irradiance increases as width decreases. A, in principle, comparable change in the irradiance distribution can also be achieved by varying the size of the microlenses, for example, that is to say by decreasing the size of the first, inner microlenses 4a in the present case.

Once again regarding the small/large microlenses 4a, b shown in FIG. 3: the arrangement such that the large microlenses 4b surround the small ones 4a can afford advantages insofar as it is thus possible for more laser diodes 2 to be provided and better arranged for the purpose of irradiating the larger irradiated area region 21b. If the arrangement were converse, that is to say the large microlenses in the center and the small ones on the outside, this would have no influence on the arrangement/position of the irradiated area regions 21a, b, however. The small irradiated area region 21a would nonetheless be situated in the large irradiated area region 21b.

The irradiation apparatus as described above may be used for motor vehicle exterior lighting, effect or operating area lighting or as a light source in a projection device, endoscope or stage spotlight.

The invention has been explained in more detail above with the aid of various embodiments, the individual features put in the context of the coordinate claims also being able to be essential to the invention in other combinations; furthermore, there is additionally no distinction drawn between the different claim categories.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. An irradiation apparatus, comprising:
 a radiation unit for the emission of radiation in the form of a beam in the time integral;
 a first microlens arrangement, downstream of the radiation unit, having a multiplicity of convergent microlenses, arranged next to one another on the same plane in relation to the direction of radiation propagation, for dividing the beam into one partial beam per convergent microlens; and
 a convergent lens, downstream of the microlens arrangement, that overlays the partial beams, at least in the time integral, in an irradiated area;
 which convergent microlenses of the first microlens arrangement break down into at least a first group and a second group having a respective plurality of convergent microlenses, wherein the convergent microlenses in each group are identical, but the convergent microlenses in the first group differ from the convergent microlenses in the second group in at least one from their shape, size and focal length, so that a first region of the irradiated area, which region is irradiated via the convergent microlenses in the first group, differs from a second region of the irradiated area, which region is irradiated by the convergent microlenses in the second group, in at least one from its shape and its size;
 wherein the convergent microlenses in the first group are irradiated at a first irradiance and the convergent microlenses in the second group are irradiated at a second irradiance, the irradiation apparatus being set up to vary the ratio of the first irradiance to the second irradiance;
 wherein the first irradiance and the second irradiance are not the same.

2. The irradiation apparatus of claim 1, wherein the convergent microlenses in at least one of the groups have the same orientation, that is to say can be transferred to one another by means of displacement.

3. The irradiation apparatus of claim 1, wherein the convergent microlenses in at least one of the groups have a rectangular shape.

4. The irradiation apparatus of claim 1, wherein the convergent microlenses in the first group differ from the convergent microlenses in the second group in their size, the small convergent microlenses being in a size ratio of at least 1:100 and no more than 9:10 in relation to the large convergent microlenses.

5. The irradiation apparatus of claim 1, wherein the convergent microlenses in the first group differ from the convergent microlenses in the second group exclusively in their size.

6. The irradiation apparatus of claim 1, wherein the convergent microlenses in at least one of the groups are parabolic.

7. The irradiation apparatus of claim 6, wherein the convergent microlenses in the first group and the convergent microlenses in the second group are parabolic.

8. The irradiation apparatus of claim 7, wherein the convergent microlenses in at least one of the groups have the same radius of curvature.

9. The irradiation apparatus of claim 1, wherein in the first microlens arrangement, the convergent microlenses in the first group are arranged in a first segment and the convergent microlenses in the second group are arranged in a second segment, the first segment being surrounded by the second segment.

10. The irradiation apparatus of claim 1, wherein in the first microlens arrangement, the convergent microlenses in the first group are mounted so as to be movable relative to the convergent microlenses in the second group.

11. The irradiation apparatus of claim 1, wherein the radiation immediately upstream of the first microlens arrangement has a beam angle and the irradiation apparatus is set up to alter the beam angle and hence the irradiance ratio.

12. The irradiation apparatus of claim 1, comprising:
 a second microlens arrangement having a multiplicity of convergent microlenses arranged next to one another on the same plane that correspond to the convergent microlenses in the first microlens arrangement in terms of their size, shape and relative arrangement in relation to one another, the second microlens arrangement being arranged downstream of the first microlens arrangement and upstream of the convergent lens such that the convergent microlenses in the first microlens arrangement each interact in pairs with those in the second microlens arrangement.

13. The irradiation apparatus of claim 1, wherein a rear focal plane of the first microlens arrangement and the front focal plane of the convergent lens coincide.

14. The irradiation apparatus of claim 1, wherein the first microlens arrangement is provided on the entry side of a basic body whose exit side, which is opposite the entry side, is planar, the convergent microlenses having a respective focus that is outside the basic body.

15. The irradiation apparatus of claim 1,
wherein the first microlens arrangement is provided on the entry side of a basic body whose exit side, which is opposite the entry side, is planar, the convergent microlenses having a respective focus that is outside the basic body, upstream of the convergent lens.

16. A method for operating an irradiation apparatus,
the irradiation apparatus comprising:
- a radiation unit for the emission of radiation in the form of a beam in the time integral;
- a first microlens arrangement, downstream of the radiation unit, having a multiplicity of convergent microlenses, arranged next to one another on the same plane in relation to the direction of radiation propagation, for dividing the beam into one partial beam per convergent microlens; and
- a convergent lens, downstream of the microlens arrangement, that overlays the partial beams, at least in the time integral, in an irradiated area;
- which convergent microlenses of the first microlens arrangement break down into at least a first group and a second group having a respective plurality of convergent microlenses, wherein the convergent microlenses in each group are identical, but the convergent microlenses in the first group differ from the convergent microlenses in the second group in at least one from their shape, size and focal length, so that a first region of the irradiated area, which region is irradiated via the convergent microlenses in the first group, differs from a second region of the irradiated area, which region is irradiated by the convergent microlenses in the second group, in at least one from its shape and its size;
- wherein the convergent microlenses in the first group are irradiated at a first irradiance and the convergent microlenses in the second group are irradiated at a second irradiance, the irradiation apparatus being set up to vary the ratio of the first irradiance to the second irradiance
- wherein the first irradiance and the second irradiance are not the same;

the method comprising:
- irradiating the convergent microlenses in the first group at the first irradiance; and
- irradiating the convergent microlenses in the second group at the second irradiance, the ratio of the first irradiance to the second irradiance being varied.

* * * * *